United States Patent [19]

McGarrity et al.

[11] Patent Number: 4,851,540
[45] Date of Patent: Jul. 25, 1989

[54] PROCESS FOR THE PRODUCTION OF BIOTIN PRECURSORS

[75] Inventors: John McGarrity; Leander Tenud; Thomas Meul, all of Visp (Kanton Wallis), Switzerland

[73] Assignee: Lonza Ltd., Gampel/Valais, Switzerland

[21] Appl. No.: 127,052

[22] Filed: Dec. 1, 1987

[30] Foreign Application Priority Data

Dec. 2, 1986 [CH] Switzerland ............ 4790/86

[51] Int. Cl.$^4$ ............... C07D 491/048; C07D 495/04
[52] U.S. Cl. ................................. 548/110; 548/111; 548/303; 549/62; 549/63; 549/295; 549/313
[58] Field of Search ................... 548/303, 110, 111

[56] References Cited

U.S. PATENT DOCUMENTS

| 2,489,232 | 11/1949 | Goldberg et al. | 548/303 |
| 2,489,235 | 11/1949 | Goldberg et al. | 548/303 |
| 4,054,740 | 10/1977 | Field | 548/303 |

FOREIGN PATENT DOCUMENTS

| 0161580 | 11/1985 | European Pat. Off. |
| 0173185 | 3/1986 | European Pat. Off. |
| 2058248 | 6/1971 | Fed. Rep. of Germany |
| 45-31699 | 10/1970 | Japan |
| 45-37775 | 11/1970 | Japan |
| 45-37776 | 11/1970 | Japan |
| 46-3580 | 1/1971 | Japan |

OTHER PUBLICATIONS

Tanaka et al., *Chem. Pharm. Bull.*, vol. 32, No. 8, pp. 3291–3298 (1984).

*Primary Examiner*—Richard A. Schwartz
*Attorney, Agent, or Firm*—Fisher, Christen & Sabol

[57] ABSTRACT

Process for the production of imidazole derivatives of the formula:

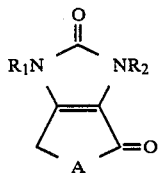

wherein $R_1$ is an (R)- or (S)-1-phenylalkyl group, an (R)- or (S)-1-alkoxycarbonyl-1-phenylmethyl group or an (R)- or (S)-1-aryloxycarbonyl-1-phenylmethyl group, $R_2$ is hydrogen, a substituted or unsubstituted alkanoyl group, an unsubstituted or a substituted benzoyl group, a substituted or an unsubstituted benzyl group, an alkoxycarbonyl group, and aryloxycarbonyl group, an alkoxyalkyl group, a pyranyl group, a substituted or unsubstituted benzenesulfonyl group, an alkylsulfonyl group, a diarylphosphinyl group, a dialkoxyphosphinyl group or a trialkylsilyl group, and A is a sulfur or oxygen atom. A tetronic acid of the formula:

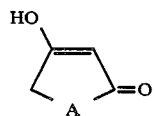

wherein A has the above-mentioned meaning, is reacted with a diazonium salt, converting the resultant arylazotetronic acid or the tautomeric arylhydrazone in a further step with a chiral amine into an arylazoamino compound, reducing the arylazoamino compound, converting the resultant diamine, with phosgene or a phosgene-equivalent reagent, into the corresponding imidazole and optionally introducing a protective group by reaction with a substituted or unsubstituted aliphatic or aromatic acid chloride, an aliphatic or aromatic carboxylic acid anhydride, a haloformic acid alkyl ester, a 1-alkoxyalkyl halide, an enol ether, an aromatic or aliphatic sulfonic acid halide, a diarylphosphinic acid halide, a phosphoric acid dialkyl ester halide, a trialkyl silyl halide or a trialkyl silyl acetamide. These imidazole derivatives are suitable as intermediate products for the production of (+) biotin.

17 Claims, No Drawings

PROCESS FOR THE PRODUCTION OF BIOTIN PRECURSORS

BACKGROUND OF THE INVENTION

1. Field of The Invention

The invention relates to new imidazole derivatives of the formula:

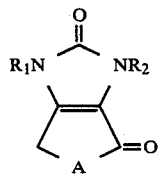

IX wherein $R_1$ is an (R)- or (S)-1-phenylalkyl group, an (R)- or (S)-1-alkoxycarbonyl-1-phenylmethyl group or an (R)- or (S)-1-aryloxycarbonyl-1-phenylmethyl group, $R_2$ is hydrogen, a substituted or unsubstituted alkanoyl group, a substituted or an ubsubstituted benzoyl group, a substituted or an unsubstituted benzyl group, an alkoxycarbonyl group, an aryloxycarbonyl group, an alkoxyalkyl group, a pyranyl group, a substituted or an unsubstituted benzenesulfonyl group, an alkylsulfonyl group, a diarylphosphinyl group, a dialkoxyphosphinyl group or a trialkylsilyl group, and A is a sulfur or oxygen atom. These compounds are suitable as intermediate products for the production of (+) biotin.

2. Background Art

A process is known from U.S. Pat. No. 2,489,232 according to which racemic biotin is produced. But since, as is known, only the optically active (+) biotin is biologically active; the thus-produced racemic biotin must then still be separated into the optical enantiomers. On the one hand, in such a case all reaction steps are performed with racemic materials, as a result of which the doubled amounts of substance must be processed. On the other hand, resolution of the racemic biotin into the corresponding enantiomers is a very complicated process, which in addition is also unprofitable, since the undesirable enantiomer practically no longer racemizes and can no longer be fed back into the process.

An improvement of such process is known from U.S. Pat. No. 2,489,235. In such improvement, the resolution of the racemates is already performed in an earlier step, but still such process has the drawback that most of the reaction steps are performed with racemic material and here too the undesirable enantiomer practically no longer racemizes and can no longer be fed back to the process.

M. Murakami et al. developed an improved process for the production of dl-biotin (cf. Japanese Published Patent Document 31669/1970, 37775/1970, 37776/1970 and 3580/1971). The improvement consists in introducing a carboxybutyl group in the 4-position of the dl-1,3-dibenzylhexahydrothioeno-[3,4-d]-imidazole-2,4-dione. Such dione is reacted with a 1,4-dihalomagnesium butane and then carboxylated with carbon dioxide.

Gerecke et al., German Published Patent Document No. 2058248, have developed a further improvement, by already producing—in an earlier step by the optical resolution of a triethylamine salt of the following formula, in which R is a cholesteryl radical, or of an ephedrine salt of the following formula, in which R is a cyclohexyl radical:

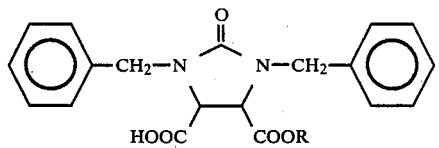

and by the further conversion with alkali metal hydrides—an optically active lactone of the formula:

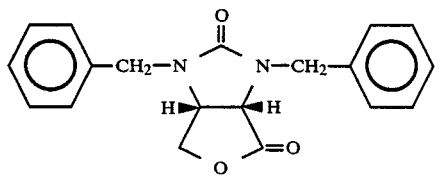

as an optically active intermediate product. A significant drawback for an industrial use of such process consists in the use of the expensive optically active compounds chloresterol and ephedrine as well as expensive alkali metal hydrides. The processes of European Published Patent Applications Nos. 0161580 and 0173185 are tainted with the same drawback, namely the use of expensive optically active compounds.

BROAD DESCRIPTION OF THE INVENTION

The object of the invention is to provide industrially simply available intermediate products, which, on the one hand, already in an earlier step relative to the total synthesis, can be optically resolved in a simple process step and, on the other hand, already exhibit in the corresponding positions the configuration of the end product.

According to the invention the object is achieved with the new imidazole derivatives of formula:

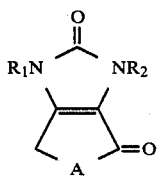

IX wherein $R_1$ is an (R)- or (S)-1-phenylalkyl group, an (R)- or (S)-1-alkoxycarbonyl-1-phenylmethyl group or an (R)- or (S)-1-aryloxycarbonyl-1-phenylmethyl group, $R_2$ is hydrogen, a substituted or unsubstituted alkanoyl group, a substituted or an unsubstituted benzoyl group, a substituted or an unsubstituted benzyl group, an alkoxycarbonyl group, and aryloxycarbonyl group, an alkoxyalkyl group, a pyranyl group, a substituted or unsubstituted benzenesulfonyl group, an alkylsulfonyl group, a diarylphosphinyl group, a dialkoxyphosphinyl group or a trialkylsilyl group, and A is a sulfur or oxygen atom.

When $R_1$ is a 1-phenylalkyl, it is preferably 1-phenyl-$(C_2-C_4)$-alkyl and most preferably 1-phenylethyl, is a 1-alkoxycarbonyl-1-phenylmethyl, it is preferably 1-$(C_1-C_4)$-alkoxy-carbonyl-1-phenylmethyl, and is a 1-aryloxycarbonyl-1-phenylmethyl, it is preferably a 1-benzyloxy-carbonyl-1-phenylmethyl- or 1-phenyloxycarbonyl-1-phenylmethyl group.

When $R_2$ is an alkanoyl, it can be $(C_1-C_4)$-alkylcarbonyl, preferably acetyl. The alkanoyl group can be substituted by halogenatoms preferably by chlorine. A preferable representative is the trichloroacetyl group. The benzoyl group and the benzyl group is preferably not substituted but substituents like halogenatoms, lower alkyl groups or lower alkoxy groups are not excluded. For example, a p-methoxybenzyl or a methylbenzyl can be applied as substituted benzyl group. When $R_2$ is an alkoxycarbonyl, it can be $(C_1–C_4)$-alkoxycarbonyl and aryloxycarbonyl, preferably phenyloxycarbonyl. When $R_2$ is an alkoxyalkyl, it is preferably $(C_1–C_4)$-alkoxymethyl. The benzolsulfonyl preferably is p-toluolsulfonyl. The alkylsulfonyl preferably is methylsulfonyl.

Generally the term alkoxy or alkyl defines an $(C_1–C_4)$-alkyl group and the term aryl defines benzyl or phenyl, preferably unsubstituted.

Suitably the compounds, which fall under formula IX are the thienoimidazole derivatives of the formula:

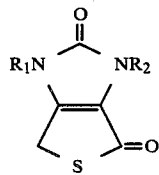

VII wherein $R_1$ and $R_2$ have the meaning set out above, and the furoimidazole derivatives of the formula:

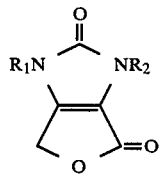

VIII wherein $R_1$ and $R_2$ have the meaning set out above.

According to the invention the compounds of formula IX, starting from a tetronic acid of the formula:

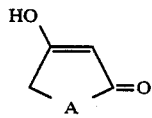

I wherein A has the meaning set out above, are produced by reaction with a diazonium salt. The resultant arylazotetronic acid or the tautomeric arylhydrazone is convered in a further step with a chiral amine into an arylazoamino compound. The process proceeds by reducing the arylazoamino compound, converting the resultant diamine, with phosgene or a phosgene-equivalent reagent, into the corresponding imidazole and optionally introducing a protective group by reaction with a substituted or unsubstituted aliphatic or aromatic acid chloride, an aliphatic or aromatic carboxylic acid anhydride, a haloformic acid alkyl ester, a 1-alkoxyalkyl halide, an enol ether, an aromatic or aliphatic sulfonic acid halide, a diarylphosphinic acid halide, a phosphoric acids dialkyl ester halide, a trialkylsilyl halide or a trialkylsilyl acetamide. This process corresponds to the following Diagram 1:

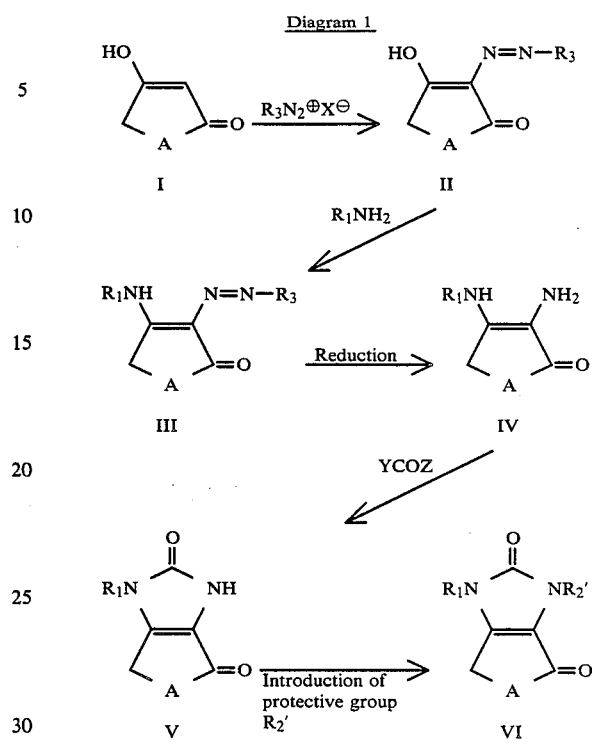

Description of Individual Process Steps:

I to II

The conversion from compound I to compound II comprises a diazo production known in itself. For A = O, i.e., for tetronic acid, the reaction was described in Tanaka et al., Chem. Pharm. Bull. 32 (1984), pp. 3291–3298.

Usually a diazonium salt of the formula is first produced, wherein $R_3$ is phenyl, unsubstituted or substituted with alkyl, haloalkyl or nitro groups or halogen atoms, and X is halogen such as chlorine, bromine or iodine, $BF_4$ or hydrogen sulfate. For this purpose, in a known way, an aniline of the formula:

$R_3NH_2$ preferably in a diluted aqueous mineral acid such as HCl, $H_2SO_2$ or $HBF_4$, is reacted with an alkali nitrite at 0° to 10° C.

The reaction can also be conducted in the presence of a polar protic solvent, such as lower alcohols or acetic acid, or with a polar aprotic solvent, such as dimethyl sulfoxide, dimethylformamide, dimethylacetamide or dimethoxyethane, or, in the case of where diazonium tetrafluoroborate is used, in acetonitrile or tetrahydrofuran. These solvents as a mixture in different ratios with water can be used.

The formed diazonium salt is then reacted to compound II with compound I, which is suitably present dissolved in water or in the above-mentioned solvents, at a temperature suitably from 0° to 40° C., preferably lower than 10° C.

It is advantageous to ensure that the pH is in a range of 4 to 7. Optionally, the pH can be adjusted to the desired range with a pH adjusting or correcting agent, such as alkali bicarbonate or a phosphate buffer for aqueous systems, or a tert-amine.

Preferably, the conversion from compound I to compound II is performed with benzenediazonium chloride in water.

The resultant phenylazotetronic acids can be present [together with their tautomeric phenylhydrazone] in different ratios to one another. Working up can take place in the usual way, preferably by separation of the product from the reaction mixture, and optionally by subsequent recrystallization.

II to III

A characteristic feature of the conversion from compound II to compound III is the introduction of an amino function in the 4-position of the heterocycle with the help of a chiral amine. As the chiral amine compounds are used of the formula:

$R_1 NH_2$ wherein $R_1$ represents an (R)- or (S)-1-phenylalkyl group or an (R)- or (S)-1-phenylalkoxycarbonylmethyl group. Preferably (R)- or (S)-1-phenylethylamine is used.

The conversion is advantageously performed in the presence of an acid catalyst. As catalysts above all Lewis acids, such as the corresponding aluminum, boron or titanium compounds, and also acids, such as methanesulfonic acid or p-toluenesulfonic acid, are suitable. Suitable Lewis acids are boron trifluoride ethyl etherate, trimethyl borate, triethyl borate, titanium tetrachloride, titanium tetraisopropoxide or aluminum chloride. The catalyst is used suitably in an amount of 1 to 50 mol percent, preferably in an amount of 1 to 20 mol percent.

Since a splitting off of water occurs with the reaction, there are suitably used as solvents either water entrainers such as toluene or benzene, or tetrahydrofuran, acetonitrile, dioxane, dimethylformamide, dimethylacetamide, chlorinated hydrocarbons such as chloroform or methylene chloride, also lower alcohols such as methanol, ethanol or propanol, suitably together with the usual drying agents such as molecular sieves, sodium sulfate, calcium sulfate or magnesium sulfate.

The work is suitably performed at a temperature between 20° and 120° C. It is also advantageous to perform the reaction in an inert gas atmosphere (e.g., nitrogen or argon).

Compound III can then be worked up and isolated according to methods known to one skilled in the art, e.g., by evaporation and subsequent recrystallization.

III to IV

The reduction of compound III to compound IV can take place either by means of a catalytic hydrogenation with hydrogen or by reaction with zinc in the presence of acetic acid or with hydrochloric acid. Preferably, the reduction is attained by means of a catalytic hydrogenation with hydrogen. Suitably platinum, palladium, rhodium, ruthenium or Raney nickel is used as the hydrogenation catalysts, optionally on a support material such as carbon, clay, pumice, aluminum oxide, aluminum silicate. Preferably platinum is used on carbon as the support material. The catalyst amount is suitably selected between 4 and 20 mol percent. The amount of catalyst on the support material can vary between 1 and 10 percent.

It is advantageous to conduct the reaction in the presence of a solvent. Acetic acid alkyl esters such as acetic acid ethyl ester, ethers such as tetrahydrofuran, dioxane or dimethoxyethane, or also dimethylformamide, dimethylacetamide, acetonitrile, acetic acid or lower alcohols are suitable. Acetic acid ethyl ester, tetrahydrofuran or ethanol are especially easy to use.

The reaction is suitably conducted at a hydrogen pressure between 1 and 50 bars, preferably between 20 and 40 bars, and at a temperature suitably between 10° and 60° C., preferably between 10° and 30° C.

After filtering off the catalyst, the reaction mixture can be worked up in the usual way, e.g., by precipitation of the product in a very nonpolar solvent.

IV to V

Compound IV is treated with phosgene or a phosgene equivalent for the formation of the imidazole.

As a phosgene equivalent, compounds are suitably used of the formula:

YCOZ wherein Y and Z are imidazolyl or chlorine, or Y is chlorine and Z is substituted or unsubstituted alkoxy, or substituted or unsubstituted aryloxy. Advantageous phosgene equivalents are the chloroformic acid lower alkyl esters, chloroformic acid phenyl ester, chloroformic acid benzyl ester or carbonyl diimidazolide.

The reaction suitably takes place in the presence of a base. Tertiary aliphatic amines, such as triethylamine, aromatic and cyclic tertiary amines, such as pyridine or diazabicylooctane, plus inorganic bases can suitably be used. But preferably tertiary aliphatic amines, such as triethylamine, are used.

Use of a base is unnecessary if compound IV is reacted with carbonyl diimidazolide as a phosgene equivalent.

It is advantageous to perform the reaction in the presence of ethers such as tetrahydrofuran or dioxane, halogenated hydrocarbons such as chloroform or methylene chloride, aromatic hydrocarbons such as toluene, carboxylic acid amides such as dimethylformamide, acetic acid alkyl esters, or also in acetonitrile as an inert organic solvent.

The reaction temperature is suitably selected in a range of 0° to 80° C.

Working up takes places in the usual way by separation of the resultant salts, evaporation of the solvent and optionally by purification of the product by, for example, a recrystallization.

V To VI

Compound V can be used by itself for stereoselective further reaction. But optionally the hydrogen atom in the 3 position of the imidazole ring can be replaced by a protective group $R_2'$.

The introduction of the protective group $R_2'$ can suitably take place by reaction of compound V with substituted or unsubstituted aliphatic or aromatic acid halides, such as, acetyl chloride, propionyl chloride, benzoyl chloride, with benzyl halides, such as benzyl chloride, with chloroformic acid esters, such as chloroformic acid ethyl ester, chloroformic acid tertbutyl ester, chloroformic acid benzyl ester or chloroformic acid phenyl ester, with phosphorus compounds, such as diphenylphosphinic acid chloride or phosphoric acid diethyl ester chloride, with aromatic or aliphatic sulfonic acid halides such as methanesulfonyl chloride, or p-toluenesulfonyl chloride, with silyl compounds, such as bis(trimethylsilyl) acetamide, or tert-butyl dimethyl silyl chloride, with alkoxyalkyl halides such as methoxymethyl chloride, or with enol ethers such as dihydropyran. Just as suitable are substituted or unsubstituted aliphatic or aromatic carboxylic acid anhydrides such as acetic anhydride.

The introduction of the protective group can take place according to known methods. Consequently, it is not gone into further.

According to this four-step process, or five-step process with the introduction of a protective group, according to the invention it is possible in a simple way and with good yields to reach intermediate product IX (compound VI or IX). This product, on the one hand, already has the skeleton of the end product and allows, in a simple way, the incorporation as the asymmetric center of biotin.

The (+) biotin can be prepared by the process wherein a compound of the formula:

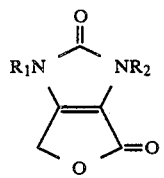   X wherein $R_1$ is an (R)- or (S)-1-phenylalkyl group, an (R)- or (S)-1-alkoxycarbonyl-1-phenylmethyl group or an (R)- or (S)-1-aryloxycarbonyl-1-phenylmethyl group, and $R_2$ is hydrogen, a substituted or unsubstituted alkanoyl group, an unsubstituted or a substituted benzoyl group, a substituted or an unsubstituted benzyl group, an alkoxycarbonyl group, aryloxycarbonyl group, an aryloxyalkyl group, an alkoxyalkyl group, a pyranyl group, an unsubstituted or substituted benzenesulfonyl group, an alkysulfonyl group, a diarylphosphinyl group, a dialkoxyphosphinyl group or a trialkylsilyl group, is catalytically hydrogenated with hydrogen, the desired diastereomer of the formula:

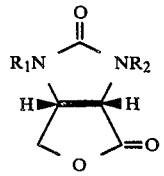   XI is separated, if $R_2$ is H, a protective group is introduced by reaction with substituted or unsubstituted aliphatic or aromatic acid chlorides, aliphatic or aromatic carboxylic acid anhydrides, haloformic acid esters, benzyl halides, 1-alkoxyalkyl halides, aromatic or aliphatic sulfonic acid halides, diarylphosphinic acid halides, phosphoric acid dialkyl ester chlorides, substituted or unsubstituted trialkylsilyl halides or substituted or unsubstituted trialkylsilyl acetamides, the desired diastereomer is converted by a further reaction with a thiocarboxylic acid salt derivative into the corresponding thiolactone, the latter thiolactone is reacted either with a Grignard reagent and subsequent splitting off of water or with a compound of the formula:

(C$_6$H$_5$)$_3$P$\oplus$(CH$_2$)$_4$COOR$_3$.X$\ominus$   XII wherein $R_3$ is H or alkyl with 1 to 4 C atoms and X represents a halogen atom, in the presence of a base to a compound of the formula:

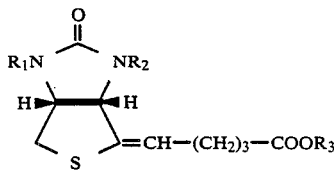   XIII wherein $R_3$ has the above-mentioned meaning, in a following step this compound is catalytically hydrogenated with hydrogen and then converted into the end product by cleavage of the protective groups.

Of crucial importance for the process in this case are the new 1H-furo[3,4-d]imidazol-2,4(3H,3aH)-diones of the formula:

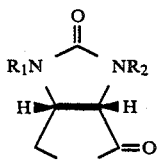   XIV wherein $R_1$ and $R_2$ have the above-mentioned meanings, but of special importance is the (3aS,6aR)-[(R)-(1-phenylethyl)]-3-benzyldihydro-1H-furo[3,4-d]imidazol-2,4(3H,3aH)-dione of the formula:

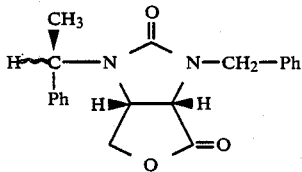   XV

DETAILED DESCRIPTION OF THE INVENTION

Example 1

(a) Production of 3-phenylazontetronic acid [3-phenylazo-4-hydroxyfuran-2(5H)-one]

300 ml of 6N hydrochloric acid solution was placed in a 1.5-liter flask equipped with a 250-ml dropping funnel, a mechanical stirrer and a thermometer. 57.6 g (0.61 mol) of distilled aniline was added with ice cooling. A solution of 43.92 g (0.64 mol) of sodium nitrite in 90 ml of ice water was added dropwise the resulting suspension and stirred for 40 min. The resultant diazonium salt solution was added dropwise to a solution of 60 g (0.6 mol) of tetronic acid and 120 g (0.88 mol) of sodium acetate trihydrate in 900 ml of water for 30 min. After this addition a yellow solid immediately precipitated. The reaction mixture was stirred at 10° C. for 1.5 hours, and filtered off; and the product was washed with 500 ml of cold methanol. It was dried at 35° C. in a vacuum. Concerning the product: Yield: 113.2 g = 92.4 percent. Melting point: 199°-200° C. (decomp.).

(b) Production of 3-phenylazo-4-[(S)-(1-phenylethylamino)]-furan-2(5H)-one 20.0 g (98 mmol) of 3-phenylazotetronic acid in 190 ml of toluene was suspended in a 500-ml three-neck flask equipped with a water separator, a thermometer and a magnetic stirrer, and was heated under argon to 80° C. Then 13.1 g (108 mmol) of (S)-phenylethylamine and 2.8 g (19 mmol) of triethyl borate were added. The solvent was refluxed under a vacuum of 300 mbar. After 7 hours, the toluene was evaporated. The black residue was washed with 100 ml of ether until a brown mass precipitated. The mass was triturated in ether and a yellowish product was obtained. The produce, 3-phenylaxo-4[(S)-(1-phenylethylamino)]-furan-2(5H)-one, was filtered off and dried in a vacuum. Concerning the product: Yield: 28.36 g = 94.0 percent. Melting point: 114°–115° C.

NMR: (CDCl$_3$, 300 MHz) δ in ppm 1.69, d, J = 7 Hz, 3H, 4,42, d, J = 16 Hz, 1H, 4.45, bm, 1H, 4.81, d, J = 16 Hz, 1H, 7.26–7.45, m, 8H, 7.78, d, J = 8 Hz, 2H, 10.55, bs, 1H.

MS: (E.I. 70 ev) m/e 307 (9%) M+, 195 (25%), 171 (11%), 126 (10%), 105 (100%), 93 (28%).

IR: (KBr) cm$^{-1}$ 3064, 3026, 1746 (s), 1621 (s), 1456, 1356, 1288, 1045, 756.

UV: (MeOH) λ max: 366 nm (ε = 21.050), 260 nm (ε = 11.540), 235 nm (ε = 12.800).

Elementary analysis for C$_{18}$H$_{17}$N$_3$O$_2$ (307.35): calculated: C 70.3%, H 5.6%, N 13.7%, found: C 70.3%, H 5.5%, N 13.4%.

[α]$_D^{25}$ [c=1 CHCl$_3$] +785°.

(c) Production of 3-amino-4[(S)-(1-phenylethylamino)]-furan-2(5H)-one 13.50 g (44 mmol) of 3-phenylazo-4-[(S)-(1-phenylethylamino)]-furan-2(5H)-one, 133 ml of acetic acid ethyl ester and 0.77 g of platinum on carbon (5 percent) were put into a 500-ml autoclave. The autoclave was closed and flushed twice with hydrogen while stirring. Then the reaction mixture was hydrogenated with hydrogen under 40 bars of pressure for 30 minutes. The catalyst was filtered off under argon and to the mother liquor was added dropwise with ice cooling, 130 ml of octane. 3-Amino-4-[(S)-(1-phenylethylamino)]-furan-2(5H)-one precipitated in the form of beige crystals. The product was dried under vacuum at room temperature. Concerning the product: Yield: 8.53 g = 89.0 percent.

Melting point: 127.5°–128.0° C.

NMR: (CDCl$_3$, 300 MHz) δ in ppm 1.55, d, J = 7.0 Hz, 3H, 2.35, bs, 2H, 4.21, d, J=15 Hz, 1H, 4.51, d, q, J=7 Hz, 7 Hz, 4.53, d, J=15 Hz 1H, 4.83, bd, J=7 Hz, 1H, 7.25–7.4, m, 5H.

MS: (E.I. 70 ev) m/e 218 (10%) M+, 114 (18%), 105 (100%).

IR: (KBr) cm$^{-1}$ 3424, 3341 (s), 1737, 1651, 1584, 1428, 700.

UV: (MeOH) λ max 283 nm (ε = 16.610).

Elementary analysis for C$_{12}$H$_{14}$N$_2$O$_2$ (218.26): calculated: C 66.0%, H 6.5%, N 12.8%, found: 66.2%, H 6.4%, N 12.8%.

[α]$_d^{25}$ [c=1 CHCl$_3$] +20.5°.

(d) Production of 1-[(S)-1-phenylethyl)]-1H-furo-[3,4-d]-imidazol-2,4(3H,6H)-dione 8.06 g (36 mmol) of 3-amino-4-[(S)-(1-phenylethylamino)]-furan-2(5H)-one and 65 ml tetrahydrofuran were placed in a 50-ml three-neck flask, which was equipped with a 50-ml dropping funnel and a magnetic stirrer, and were cooled to 0° C. Then a solution of 5.78 g (36 mmol) of chloroformic acid phenyl ester in 10 ml of tetrahydrofuran and a solution of 3.78 g (36 mmol) of triethylamine in 10 ml of tetrahydrofuran were added at the same time for 40 minutes. The white suspension was filtered and the light brown mother liquor was evaporated. The residue, a brown foam, was dissolved in 60 ml of acetonitrile and this solution was added in 40 minutes to a solution of 3.78 g (36 mmol) of triethylamine in 40 ml of acetonitrile, which was refluxed. The reaction mixture was evaporated and the residue washed with 50 ml of ether. The beige product, [1-(S)-(1-phenylethyl)]-1H-furo[3,4-d]-imidazol-2,4(3H,6H)-dione, was filtered off and dried in a vacuum. After recrystallization in methanol the product yield was 5.75 g=66.0 percent. Concerning the product: Melting point: 159.5°–160° C.

NMR: (CDCl$_3$, 300 MHz) in ppm 1.77, d, J = 7 Hz, 3H, 4.07, d, J = 16 Hz, 1H, 4.72, d, J = 16 Hz, 1H, 5.57, q, J = 7 Hz, 1H, 7.35–7.58, m, 5H, 9.75, bs, 1H.

MS: (E.I. 70 ev) m/e 244 (16%), 105 (100%), 77 (37%).

IR: (KBr) cm$^{-1}$ 3250, 2981, 1761, 1700, 1482, 1450, 1340, 1268, 1000, 739, 705.

UV: (MeOH) λ max 266 nm (ε = 12.900).

Elementary analysis for C$_{13}$H$_{12}$O$_2$N$_2$ (244.25): calculated: C 63.9%, H 4.9%, N 11.5%, found: C 63.6%, H 4.9%, N 11.3%.

[α]$_D^{25}$ [c=1 CHCl$_3$] −69.5°.

EXAMPLE 2

(a) Production of 3-phenylazothiotetronic acid

[3-phenylazo-4-hydroxythiophen-2(5H)-one or 2,3,4-trioxotetrahydrothiophene-3-phenylhydrazone]

28 ml of 6N hydrochloric acid solution was placed in a 100-ml beaker, which was equipped with a 100-ml dropping funnel, a thermometer and a mechanical stirrer. 5.02 g (53.9 mmol) of aniline was added with ice cooling. Then a solution of 3.81 g (55.2 mmol) of sodium nitrite in 21 ml of ice water was added dropwise to the resulting suspension in 30 min. with vigorous stirring. The resultant diazonium salt solution was added dropwise to a solution of 5.78 g (50 mmol) of thiotetronic acid in 49 ml of 1N sodium hydroxide solution at 5° C. with vigorous stirring in 30 minutes. At the same time 55 ml of 1N sodium carbonate solution was added to keep the pH of 7.0 constant. The mustard yellow product was filtered off, washed with 30 ml of water and dried in a vacuum. After recrystallization in toluene, the product yield was 10.5 g = 95.0 percent. Concerning the product: Melting point: 195°–196.5° C.

NMR: (CDCl$_3$, 300 MHz) δ in ppm 3.89, s, 2H, 3.95, s, 1H, 7.32, t, J=7 Hz, 2H, 7.46, t, J=7 Hz, 2H, 7.58, d, J=7 Hz, 2H, 3.89, s, 2H, 6.67, s, 1H, 7.32, t, J=7 Hz, 1H, 7.45, t, J=7 Hz, 2H, 7.57, d, J=7 Hz, 2H.

The tautomer ratio of 3-phenylazothiotetronic acid to 2,3,4-trioxotetrahydrothiophene-3-phenylhydrazone is 3 to 1.

MS: (E.I. 70 ev) m/e 220 (70%) M+, 143 (13%), 105 (31%) 92 (30%), 77 (100%).

IR: (KBr) cm$^{-1}$ 3450, 1688, 1673 s, 1532 s, 1465, 1424, 1397 s, 1129 s, 912 s, 764 s.

UV: (MeOH) λ max 408 nm (ε=14.100), 372 (ε=16.700), 235 nm (ε—6.670).

Elementary analysis for C$_{10}$H$_8$N$_2$O$_2$S (220.25): calculated: C 54.5%, H 3.7%, N 12.7%, S 14.6%, found: C 54.3%, H 3.5%, N 12.7%, S 14.8%.

(b) Production of 3-phenylazo-4-[(S)-(1-phenylethylamino)]-thien-2(5H)-one 6.56 g (29.8 mmol) of 3-phenylazothiotetronic acid was dissolved in 165 ml of toluene with reflux under nitrogen in a 250-ml three-neck flask, which was equipped with a water separator, jacketed coil condensor and magnetic stirrer. Then 14.53 g (119.9 mmol) of (S)-1-phenylethylamine was added and then in 40 minutes a solution of 2.19 g of boron trifluoride ethyl etherate in 5 ml of toluene was added. The reaction mixture was allowed to cool to room temperature. This reaction mixture was extracted with 100 ml of 0.9N hydrochloric acid, then with 50 ml of saturated sodium bicarbonate solution and then with 50 ml of saturated sodium sulfate solution. The dark brown solution was dried over 20 g of magnesium sulfate and evaporated. 50 ml of ether was added to the brown, viscous residue and allowed to rotate under slight vacuum. The resultant solid was dissolved in 6 ml of dichloromethane with reflux and recrystallized after the addition of 14 ml of ether at 0° C. After another recrystallization, the yield of 3-phenylazo-4-[(S)-(1-phenylethylamino)]-thien-2(5H)one was 5.59 g=58 percent. Concerning the product: Melting point 129°–130° C.

NMR: (CDCl3, 300 MHz) δ in ppm 1.71, d, J = 7 Hz, 3H, 3.64, d, J=17 Hz, 1H, 3.98, d, J=17 Hz, 1H, 4.77, d, q, J=7 Hz, 7 Hz, 1H, 7.25–7.5, m, 8H, 7.76, d, J=8 Hz, 2H, 12.34, bs, 1H.

MS: (E.I. 70 ev) m/e 323 (10%) M+, 195 (22%), 105 (100%), 93 (30%), 77 (25%).

IR: (KBr) cm$^{-1}$ 3500 b, 1720, 1600 s, 1580 s, 1450, 1280.

UV: (MeOH) λ max 410 nm (ε=9.600), 375 nm (ε=21.910), 290 nm (ε=11.880), 231 nm (ε=13.823).

Elementary analysis for C18H17N3OS (323.41): calculated: C 66.8%, H 5.3%, N 13.0%, S 9.9%, found: C 66.7%, H 5.2%, N 13.2%, S 9.5%.

[α]$_D^{25}$ [c=1 CHCl3] +889°.

(c) Production of 3-amino-4-[(S)-1(1-phenylethylamino)]-thien-2(5H)-one

A solution of 5.0 g (15.5 mmol) of 3-phenylazo-4-[(S)-(1-phenylethylamino)]-thien-2(5H)-one in 30 ml of tetrahydrofuran was placed in a 100-ml autoclave. Then 0.49 g of platinum on carbon 5 percent was added. The autoclave was flushed twice and the solution was hydrogenated with a hydrogen pressure of 30 bars for 45 minutes. The catalyst was filtered off under argon and to the mother liquor was added 90 ml of hexane with ice cooling. 3-Amino-4-[(S)-(1-phenylethylamino)]-thien-2(5H)-one precipitated as a beige, viscous oil. Concerning the product: Yield: 2.4 g=65.0 percent.

NMR: (CDCl3, 300 MHz), δ in ppm 1.54, d, J=7 Hz, 3H, 3.30, bs, 3-4H, 3.37, d, J=16.5 Hz, 1H, 3.72, d, J = 16.5 Hz, 1H, 4.60, q, J=7 Hz, 1H, 7.22–7.37, m, 5H.

MS: (E.I. 70 ev) m/e 234 (4%), M+, 130 (18%), 105 (100%).

(d) Production of (S)-(1-phenylethyl)-1H-thieno-[3,4-d]-imidazol-2,4(3H,6H)-dione 22 ml of tetrahydrofuran was placed in a 250-ml three-neck flask equipped with two 50-ml dropping funnels, a thermometer and a magnetic stirrer. It was cooled to 0° C. and 11.1 ml of 1.25M phosgene solution in toluene (13.87 mmol) was added under argon. Simultaneously was added a solution of 3.24 g (13.82 mmol) of 3-amino-4-[(S)-(1-phenylethylamino)]-thien-2(5H)-one in 10 ml of tetrahydrofuran and a solution of 2.18 g (27.75 mmol) of triethylamine in 10 ml of tetrahydrofuran was added in 3 hours at 5° C. To it was added 10 ml of 5 percent aqueous ammonia solution. The tetrahydrofuran was evaporated and the aqueous residue was extracted three times with 10 ml of dichloromethane. The solution was evaporated and chromatographed by 100 g of silica gel with 700 ml of ethyl acetate. The yield of (S)-(1-phenylethyl)-thieno[3,4-d]-imidazol-2,4(3H,6H)-dione (beige crystals) was 2.16 g=60 percent.

Melting point: 218°–220° C.

NMR: (CDCl3, 300 MHz) δ in ppm 1.83, d, J=7 Hz, 3H, 3.23, d, J=16.5 Hz, 1H, 3.86, d, J=16.5 Hz, 1H, 5.73, q, J=7 Hz, 1H, 7.40, m, 5H, 8.78, bs, 1H.

MS: (E.I. 70 ev) m/e 260 (4%) M+, 156 (4%), 105 (100%), 79 (105), 77 (12%).

IR: (KBr) cm$^{-1}$ 3223, 2945, 2918, 1702 s, 1619, 1451, 1351, 1268.

UV: (MeOH) λ max 297 nm (ε=9.805), 248 nm (ε —5.960).

Elementary analysis for C13H12N2O2S (260.31): calculated: C 60.0%, H 4.7%, N 10.7%, S 12.3%, found: C 59.6%, H 4.7%, N 10.8%, S 12.0%.

[α]$_D^{25}$ [c=1 CHCl3] −63.2°.

(e) Production of 1-[(S)-(1-phenylethyl)]-3-acetyl-1H-thieno[3,4-d]imidazol-2,4(3H,6H)-dione 0.5 g (1.94 mmol) of 1-[(S)-(1-phenylethyl)]-1H-thieno-3,4-d]-imidazol-2,4(3H,6H)-dione in 20 ml of acetic acid anhydride was heated in a 25-ml flask at 50° C. for 3 hours. Then the solvent was evaporated and the residue washed with 3 ml of ether. The beige product was then dried. The yield of 1-[(S)-(1-phenylethyl)]-3-acetyl-1H-thieno-[3,4-d]imidazol-2,4(3H,6H)-dione was 0.43 g=73.0 percent. Concerning the product: Melting point 187°–189.5° C.

NMR: (CDCl3, 300 MHz) δ in ppm 1.85, d, J=7 Hz, 3H, 2.71, s, 3H, 3.18, d, J=17.5 Hz, 1H, 3.83, d, J=17.5 Hz, 1H, 5.71, q, J=7 Hz, 1H, 7.35–7.45, m, 5H.

MS: (E.I. 70 ev) m/e 302 (1%) M+, 260 (10%), (—CH2CO), 165 (5%), 105 (100%), 43 (20%).

IR: (KBr) cm$^{-1}$ 2920, 1736 s, 1447, 1376, 1354, 1298.

UV: (MeOH) λ max 297 nm (ε=11.480), 248 nm (ε=6.930).

Elementary analysis for C15H14O3N2S (302.35): calculated: C 59.6%, H 4.7%, N 9.3%, S 10.6%, found: C 58.9%, H 4.7%, N 9.2%, S 10.3%.

[α]$_D^{25}$ [c=1 CHCl3] −63.3°.

Example 3

Production of 1-[(S)-(1-phenylethyl)]-3-benzyl-1H-thieno[3,4-d]imidazol-2,4(3H,6H)-dione To a suspension of 75 mg (3.1 mmol) of sodium hydride in 15 ml of tetrahydrofuran were added 0.73 g (2.8 mmol) of 1-[(S)-(1-phenylethyl)]-1H-thieno[3,4-d]imidazol-2,4(3H,6H)-dione, 0.54 g (3.2 mmol) of benzyl bromide and 10 ml of diethylene glycol diethyl ether. The reaction mixture was refluxed for 12 hours. The solvent was evaporated in a vacuum and the residue separated between 10 ml of dichloromethane and 10 ml of water. The aqueous phase was washed twice with 10 ml of dichloromethane. The organic phases were combined, dried with 10 g of magnesium sulfate and evaporated. The solid residue was washed with 5 ml of ether, filtered off and dried. The yield of 1-[(S)-(1-phenylethyl)]-3-benzyl-1H-thieno[3,4-d]imidazol-2,4(3H,6H)-dione was 57.0 mg=60 percent. Concerning the product: Melting point: 143°–145° C.

NMR: (CDCl$_3$, 300 MHz) δ in ppm 1.79, d, J=7 Hz, 3H, 3.18, d, J=17 Hz, 1H, 3.78, d, J=17 Hz, 1H, 5.03, s, 2H, 5.21, J=7 Hz, 1H, 7.27–7.4, m, 8H, 7.49, d, J=8 Hz, J=1.5 Hz, 2H.

MS: (E.I. 70 ev) m/e 350 (4%) M$^-$, 246 (12%), 105 (100%), 91 (40%).

IR: (KBr) cm$^{-1}$ 2982, 1707 s, 1672 s, 1456, 1346, 846, 700.

UV: (MeOH) λ max 285.8 nm (ε=10.200).

Example A (1) Production of (3as,6aR)-1-[(R)-(1-phenylethyl)]-dihydro-1H-furo[3,4-d]imidazol-2,4(3H,3aH)-dione A solution of 8.98 g (36.8 mmol) of 1-[(R)-(1-phenylethyl)]-1H-furo[3,4-d]imidazol-2,4(3H,6H)-dione in 90 ml of dimethylformamide was placed in a 250-ml autoclave and 0.90 g of Rh/Al$_2$O$_3$ (5 percent) is added. Then the autoclave was flushed twice successively with hydrogen, and filled to 40 bars. The mixture was stirred for 10 hours. Then the catalyst was filtered off. The solvent was evaporated at 13.3 mbar and the residue was crystallized with 10 ml of ethyl acetate. (3aS,6aR)-1[(R)-(1-phenylethyl)]-dihydro-1H-furo[3,4-d]imidazol-2,4(3H,3aH)-dione was obtained as a white crystalline product in a yield of 4.89 g=54 percent. Concerning the product: Melting point: 153°–154° C.

$^1$H-NMR: (CDCl$_3$, 300 MHz) δ 1.61, d, J=7Hz, 3H, 3.45, dd, J=10.5 Hz, 1,4 Hz, 1H, 3.95, dd, J=10.5 Hz, 5Hz, 17H, 4.21, d, J=9.5 Hz, 1H, 4.57, ddd, J=10.5 Hz, 9.5 Hz, 1.4 Hz, 71H, 5.24, bs, 1H, 5.31, q, J=7 Hz, 1H, 7.4, m, 5H.

MS: (E.I. 70 ev) m/e 246 (30%) M$^+$, 231 (45%), 161 (28%), 105 (100%).

IR: (KBr) cm$^{-1}$ 3388, 1771 (s), 1669 (s), 1422, 1255, 699.

UV: (MeOH) λ max 372 nm (ε=119), 256 nm (ε=764).

Elementary analysis for C$_{13}$H$_{14}$N$_2$O$_3$ (246.27): calculated: C 63.1%, H 5.7%, N 11.3%, found: C 63.4%, H 5.7%, N 11.4%.

[α]$_D^{20}$ [c=1 CHCl$_3$]+211.7°.

(2) Production of (3aS,6aR)-1-[(S)-(1-phenylethyl)]-dihydro-1H-furo[3,4-d]imidazol-2,4(3H,3aH)-dione A solution of 3.7 g (15.16 mmol) of 1-[(S)-(1-phenylethyl)]-1H-furo[3,4-d]imidazol-2,4(3H,6H)-dione in 100 ml of acetic acid is placed in a 250-ml autoclave and 0.4 g of palladium on activated carbon (5 percent) was added. Then the autoclave was flushed twice successively with hydrogen and filled to 50 bars. This mixture was stirred for 15 hours at room temperature. The catalyst was then filtered off. The solvent was evaporated at 20 mbars and the residue was chromatographed over silica gel with ethyl acetate. 2.0 g (54 percent yield) of the title product was eluted. Recrystallization in methanol yields white needles. Concerning the product: Melting point: 123°–125° C.

$^1$H-NMR: (CDCl$_3$, 300 MHz) δ 1.65, d, J=7.4 Hz, 3H, 4.08, d, J=8.6 Hz, 1H, 4.12, m, 1H, 4.37, dd, J=10.3 Hz, 4.8 Hz, 1H, 4.48, dd, J =10.2 Hz, 1.3 Hz, 1H, 5.36, q, J=7.3 Hz, 1H, 5.48, s, 1H.

MS: (E.I. 70 ev) m/e 246 (30% M$^+$, 231 (45%), 161 (28%), 105 (100%).

[α]$_D^{20}$ [c=0, CHCl$_3$] −6.7%.

Subsequently, the [3aR,6aS] isomer was eluted in a yield of 1.05 g (28 percent).

Example B (1) Production of (3aS,6aR)-1-[(R)-(1-phenylethyl)]-3-benzyl-dihydro-1H-furo[3,4-d]imidazol-2,4(3H, 3aH)-dione 48 ml of dimethoxyethane and 0.39 g (16.2 mmol) of sodium hydride were placed in a 100-ml three-neck flask equipped with a magnetic stirrer under argon and with complete exclusion of moisture. Then 3.24 g (13.2 mmol) of (3aS,6aR)-1-[(R)-(1-phenylthyl)]-dihydro-1H-furo[3,4-d]imidazol-2,4(3H,3aH)-dione was added. After a stirring time of 10 min., 2.76 g (16.2 mmol) of benzyl bromide was added and the suspension was stirred for 30 min. Then the reaction mixture was evaporated. The residue was dissolved with 25 ml of dichloromethane and 25 ml of water. The phases were separated and the aqueous phase was washed three times, each time with 15 ml of dichloromethane. The organic phases were combined, dried with 5 g of magnesium sulfate and evaporated. (3aS,6aR)-1-[(R)-(1-phenylethyl)]-3-benzyl-dihydro-1H-furo[3,4-d]-imidazol-2,4(3H,3aH)-dione was obtained as a beige product in a yield of 3.56 g (80.5 percent). Concerning the product: Melting point: 163°–164.5° C.

$^1$H-NMR: (CDCl$_3$, 300 MHz) δ 1.58, d, J=7 Hz, 3H, 3.38, dd, J=10 Hz, 3 Hz, 1H, 3.82, dd, J=10 Hz, 5 Hz, 1H, 3.89, d, J=9 Hz, 1H, 4.32, d, J=15 Hz, 1H, 4.44, ddd, J=9 Hz, 5 Hz, 3 Hz, 1H, 5.05, d, J=15 Hz, 1H, 5.36, q, J=7 Hz, 1H, 7.30–7.41, m 10H.

MS: (E.I. 70 ev) m/e 336 (26%) M$^+$, 321 (9%), 231 (22%), 187 (16%), 174 (14%), 105 (56%), 91 (100%).

Elementary analysis for C$_{20}$H$_{20}$N$_2$O$_3$ (336.39): calculated: C 71.4%, H 6.0%, N 8.3%, found: C 71.3%, H 6.2%, N 8.3%.

[α]$_D^{20}$ [c=0.5 CHCl$_3$]+122.3°.

(2) Production of (3aS,6aR)-1-[(R)-(1-phenylethyl)]-3-(4-methoxybenzyl)-dihydro-1H-furo[3,4-d]-imidazol-2,4(3H,3aH)-dione 9.75 g (0.22 mol) of sodium hydride (55 percent in oil) was added in 10 portions in 2 hours at −10° C. under argon to a solution of 50.0 g (0.2 mol) of (3aS,6aR)-1-[(R)-(1-phenylethyl)]-dihydro-1H-furo[3,4-d]imidazol-2,4(3H,3aH)-dione and 39.8 g (0.25 mol) of 4-methoxybenzyl chloride in 500 ml of dried N,N-dimethylformamide. The reaction mixture was stirred at 5° C. for 2 hours and then at room temperature for another 2 hours. Then 8 ml of acetic acid was added. Then the mixture was evaporated to dryness. Then the residue was taken up in 100 ml of water and 200 ml of dichloromethane, the phases were separated and the aqueous phase was extracted twice with 100 ml of dichloromethane. The organic phases were dried over magnesium sulfate and concentrated. After suspension in ethanol with refluxing, cooling and filtering, 53.5 g (72 percent) of the title product was obtained in the form of white needles. Concerning the product: Melting point: 146.1°–146.4° C.

¹H-NMR: (CDCl₃, 300 Hz) δ 1.58, d, J=7 Hz, 3H, 3.37, dd, J=10 Hz, 3 Hz, 3H, 3.82, s, 3H, 3.82, dd, J=10 Hz, 5.5 Hz, 1H, 3.88, d, J=8.5 Hz, 1H, 4.25, d, J=14.5 Hz, 1H, 4.34, ddd, J=8.5 Hz, 5.5 Hz, 3H, 4.97, d, J=14.5 Hz, 1H, 5.734, q, J=7 Hz, 1H, 6.88, d, J=8.5 Hz, 2H, 7.32–7.38, m, 7H.

[α]$_D^{20}$ [c=1 CHCl₃]+104.7°.

(3) Production of (3aS,6aR)-1-[(R)-(1-phenylethyl)]-3-tert-butoxycarbonyl-dihydro-1H-furo[3,4-d]-imidazol-2,4(3H,3aH)-dione 3.83 g (88 mmol) of sodium hydride (55 percent in oil) was added in 10 portions in 2 hours at −10° C. under argon to a solution of 20.0 g (81 mmol) of (3aS,6aR)-1-[(R)-(1-phenylethyl)]-dihydro-1H-furo[3,4-d]-imidazol-2,4(3H,3aH)-dione and 21.3 g (97 mmol) of di-tert-butyldicarbonate in 200 ml of dried N,N-dimethylformamide. The reaction mixture was stirred at 5° C. for 2 hours and then at room temperature for another 2 hours. Then 1 ml of acetic acid was added. Then the mixture was evaporated to dryness. The residue was taken up in 50 ml of water and 100 ml of dichloromethane, the phases were separated and the aqueous phase was extracted twice with 100 ml of dichloromethane. The organic phases were dried over magnesium sulfate and concentrated. After suspension in ethanol under fluxing, cooling and filtering, 25.8 g (92 percent) of the title produce was obtained in the form of white needles. Concerning the product: Melting point: 177.4°–178.1° C.

¹H-NMR: (CDCl₃, 300 MHz) δ 1.59, s, 9H, 1.63, d, J=7.5 Hz, 3H, 3.51, d, J=11 Hz, 1H, 3.97, dd, J=11 Hz, 5 Hz, 1H, 4.50, dd, J=8 Hz, 5 Hz, 1H, 4.90, d, J=8 Hz, 1H, 5.39, q, J=7.5 Hz, 1H, 7.3–7.4, m, 5H.

[α]$_D^{20}$ [c=1 CHCl₃]+55.8°.

Production of (3aS,6aR-1-[(R)-(1-phenylethyl)]-3-methoxymethyl-dihydro-1H-furo[3,4-d]-imidazol-2,4(3H,3aH)-dione 4.0 g (93 mmol) sodium hydride (55 percent in oil) was added in 10 portions in 2 hours at −10° C. under argon to a solution of 19 g (77 mmol) of (3aS,6aR)-[(R)-(1-phenylethyl)]-dihydro-1H-furo[3,4-d]imidazol-2,4(3H,3aH)-dione and 9.42 g (120 mmol) of chloromethyl methyl ether in 200 ml of dried N,N-dimethylformamide. The reaction mixture was stirred at 5° C. for 2 hours and then at room temperature for another 2 hours. Then 2 ml of acetic acid was added. Then the mixture was evaporated to dryness. Then the residue was taken up in 50 ml of water and 100 ml of dichloromethane, the phases were separated and the aqueous phase was extracted twice with 100 ml of dichloromethane. The organic phases were dried over magnesium sulfate and concentrated. After chromatographing the oily residue over silica gel with 500 ml of dichloromethane ethyl acetate and concentration of the fractions, 4.0 g (18 percent) of the title product was obtained as white powder. Concerning the product: Melting point: 96°–98° C.

¹H-NMR: (CDCl₃, 300 MHz) δ 1.61, d, J=7.5 Hz, 3H, 3.36, s, 3H, 3.41, dd, J=10 Hz, 3 Hz, 1H, 3.89, dd, J=10 Hz, 6 Hz, 1H, 4.36, d, J=9 Hz, 1H, 4.52, ddd, J=9 Hz, 6 Hz, 3 Hz, 1H, 4.87, d, J=11 Hz, 1H, 4.97, d, J=11 Hz, 1H, 5.34, q, J =7.5 Hz, 1H, 7.35–7.4, m, 5H.

Example C

Production of (3aS,6aR)-1-[(R)-(1-phenylethyl)]-3-benzyl-dihydro-1H-thieno[3,4-d]-imidazol-2,4(3H,3aH)-dione 2.03 g (6.03 mmol) of (3aS,6aR)-1-[(R)-(1-phenylethyl)]-3-benzyl-dihydro-1H-furo-[3,4-]-imidazol-2,4(3H,3aH)-dione dissolved in 2 ml of dimethylacetamide was placed in a 25-ml flask, equipped with a magnetic stirrer and a ball condenser. The solution was heated in 150° C. and 0.81 g (7.14 mmol) of potassium thioacetate was added. After 45 min. the reaction mixture was allowed to cool and treated with 40 ml of toluene and 40 ml of water. The phases were separated; the toluene phase was washed three times with 20 ml of water and the combined aqueous phases were washed three times, each time with 30 ml of toluene. The toluene phases were combined, dried and evaporated. The resulting brown solid was washed with 5 ml of ether. Then the beige product, (3aS,6aR)-1-[(R)-(1-phenylethyl)]-3-benzyl-dihydro-1H-thieno[3,4-d]-imidazol-2,4(3H,3aH)-dione was filtered off and dried. Concerning the products: Yield: 1.82 g=85 percent.

Melting point: 144°–145° C.

¹H-NMR: (CDCl₃, 300 MHz) δ 1.67, d, J=7 Hz, 3H, 2,71, dd, J=12.5 Hz, 2.5 Hz, 1H, 3.03, dd, J=12.5 Hz, 5 Hz, 1H, 3.81, d, J=8 Hz, 1H, 4.34, d, J=15 Hz, 1H, 4.40, ddd, J=8 Hz, 5 Hz, 2.5 Hz, 1H, 5.04, d, J=15 Hz, 1H, 5.41, q, J =7 Hz, 1H, 7.30–7.50, m, 10H.

MS: (E.I. 70 ev) m/e 352 (1%) M⁺, 324 (30%), 278 (35%), 174 (80%), 146 (30%), 105 (70%), 91 (100%).

Elementary analysis for C₂₀H₂₀N₂O₂S (352.46): calculated: C 68.2%, H 5.7%, N 7.9%, S 9.1%, found: C 67.9%, H 5.9%, N 8.0%.

[α]$_D^{20}$ [c=1.5 CHCl₃]+128.5°.

Example D

Production of (3aS,6aR)-hexahydro-1-[(R)-(1-phenylethyl)]-2-oxo-3-benzylthieno[3,4-d]-imidazol-4-ylidene pentanoic acid 159.8 mg (3.66 mmol) of sodium hydride and 1.7 ml of dimethyl sulfoxide were placed in a 25-ml round-bottom flask. The suspension was heated with stirring and under argon to 70° C. It was stirred for 40 minutes more until evolution of hydrogen was complete. The solution was cooled to room temperature and a solution of 801.5 mg (1.8 mmol) of (4-carboxybutyl)-triphenylphosphonium bromide in 1 ml of dimethyl sulfoxide was added. The dark red reaction mixture was stirred for 15 minutes and then added dropwise to a solution of 271 mg (0.77 mmol) of (3as,6aR)-1-[(R)-(1-phenylethyl)]-3-benzyl-dihydro-1H-thieno[3,4-d]-imidazol-2,4(3H,3aH)-dione in 2 ml of dimethyl sulfoxide and 0.2 ml of toluene. The reaction mixture was stirred for 2 hours at room temperature. Then 1 g of ice, 1 ml of conc, HCl and again 9 g of ice were added. After 5 minutes, 5 ml of water, 10 ml of benzene and 5 ml of ethyl acetate were added. Then the mixture was stirred for 1 hour at 60° C. The phases were separated. The brown organic phase was dried with 5 g of magnesium sulfate and separated with 4 preparative silica gel thin-layer plates (1 mm) by means of ethyl acetate. The product, (3aS, 6aR)-hexahydro-1-[(R)-(1-phenylethyl)]-2-oxo-3-benzylthieno[3,4-d]-imidazol-4-ylidene pentanoic acid, a colorless oil, was obtained in a yield of 38.2 mg (12 percent). Concerning the product:

¹H-NMR: (CDCl₃, 300 MHz) δ 1.58, d, J=7 Hz, 3H, 1,59, q, J=7 Hz, 2H, 1.98, m, 2H, 2.22, t, J=7.5 Hz, 2H, 2.29, dd, J=11.5 Hz, 4 Hz, 1H, 2.41, dd, J=11.5 Hz, 5 Hz, 1H, 3.97, d, J=15 Hz, 1H, 4.18, m, 2H, 4.84, d, J=15 Hz, 1H, 5.30, q, J=7 Hz, 1H, 5.31, t, J=7 Hz, 1H, 7.10–7.40, m, 10H.

MS: (E.I. 70 ev) m/e 436 (55%) M⁺, 331 (55%), 252 (32%), 237 (60%), 120 (40%), 106 (100%).

(2) Production of (3aS,6aR)-hexahydro-1-[(R)-(1-phenylethyl)]-2-oxo-3-benzylthieno[3,4-d]imidazol-4-ylidene pentanoic acid 0.802 g (33 mmol) of magnesium chips were put into 5 ml of tetrahydrofuran. Then 2.37 g (11 mmol) of dibromobutane in 30 ml tetrahydrofuran was added in 1 hour. The reaction mixture was refluxed for 2 hours, then 2.55 g (22 mmol) of tetramethylethylenediamine was added and refluxed for another hour. To the suspension, cooled to 0° C., was then added 3.52 g (10 mmol) of (3aS,6aR)-1-[(R)-(1-phenylethyl)]-3-benzyl-dihydro-1H-thieno[3,4-d]imidazol-2,4(3H,3aH)-dione in 50 ml of tetrahydrofuran. Then the reaction mixture was stirred for 2 hours at room temperature and then cooled to °0 C. Carbon dioxide gas was introduced in 1 hour at 0° C. and 1 hour at room temperature. The reaction mixture was poured onto a mixture of 85 g of ice and 11.5 ml of conc. hydrochloric acid and then extracted with ethyl acetate. The combined organic phases were washed with water and saturated sodium chloride solution, dried with magnesium sulfate and finally concentrated. 50 mg of p-toluenesulfonic acid was added to the residue, which was then taken up in 170 ml of toluene. The reaction water was refluxed and distilled off by means of a water separator. The remaining toluene solution was concentrated and the resulting oil was chromatographed over silica gel with acetic acid ethyl ester/toluene. 1.22 g (28 percent) of the title product was obtained as a light yellowish oil.

(3) Production of (3aS,6aR)-hexahydro-1-[(R)-(1-phenylethyl)]-2-oxo-3-benzylthieno[3,4-d]imidazol-4-ylidene pentanoic acid 8.6 g of magnesium chips was placed in 75 ml of tetrahydrofuran. Then a mixture of 3.2 g of 1,2-dibromoethane and 2.5 g of 1,4-dichlorobutane in 35 ml of tetrahydrofuran was added within 15 minutes so that the temperature could be kept between 30° and 35° C. Then another b 20.5 g of 1,4-dichlorobutane in 75 ml of tetrahydrofuran was added within 30 minutes. The reaction mixture was stirred for 3 hours at this temperature and then mixed with 9 g of tetramethylethylenediamine and 180 ml of tetrahydrofuran. The reaction solution was cooled to −40° to −45° C. and then mixed with a solution of 30 g of (3aS,6aR)-1-[(R)-(1-phenylethyl)]-3-benzyl-dihydro-1H-thieno[3,4-d]imidazol-2,4(3H,3aH)-dione in 180 ml of tetrahydrofuran within 20 minutes. It was stirred at this temperature for 1 hour and then CO₂ gas was introduced for 30 minutes. The reaction mixture was poured onto 400 ml of 10 percent aqueous sulfuric acid and extracted several times with toluene. The toluene phase was mixed with 0.8 g of conc. sulfuric acid, washed with water and concentrated on a rotary evaporator. The residue was mixed with 400 ml of 10 percent potassium carbonate solution and extracted with ethyl acetate. The organic phase was washed again with 10 percent potassium carbonate solution. The combined aqueous phases were adjusted to pH 7.3 with aqueous sulfuric acid and extracted several times with ethyl acetate. The organic phase was finally dried with magnesium sulfate and concentrated. The product was precipitated by addition of hexane, filtered off and dried. 32.5 g (89.3 percent) of the title product was obtained as snow-white powder with a content (HPLC) of more than 99 percent. Concerning the product: Melting point: 101.0°–102.0° C.

$[\alpha]_D^{20}$ [c=1.0 methanol] +2.53.8°.

Example E (e) Production of (3aS,6aR)-hexahydro-1-[(R)-(1-phenylethyl)]-2-oxo-3-benzylthieno[3,4-d]imidazol-4-yl pentanoic acid A solution of 78.6 mg of (3aS,6aR)-hexahydro-1-[(R)-(1-phenylethyl)]-2-oxo-3-benzylthieno[3,4-d]imidazol-4-ylidene pentanoic acid in 5 ml of isopropanol was placed in a 100-ml autoclave and 39 mg of palladium (5 percent) on carbon was added. The autoclave was flushed twice with hydrogen and the mixture was stirred under 50 bars of hydrogen pressure at 50° C. for 24 hours. Then the catalyst was filtered off and the solvent evaporated off. The product, (3aS,6aR)-hexahydro-1-[(R)-(1-phenylethyl)]-2-oxo-3-benzylthieno[3,4-d]imidazol-4-ylidene pentanoic acid, was obtained as a colorless oil in a yield of 56.1 mg (72 percent). Concerning the product:

¹H-NMR: (CDCl₃, 300 MHz) δ 1.57, m, 6H, 1.61, d, J=7 Hz, 3H, 2.13, m, 1H, 2.33, m, 2H, 3.03, m, 1H, 3.90, dd, J=10 Hz, 5 Hz, 1H, 3.94, d, J=15 Hz, 1H, 4,22, m, 1H, 5.06, d, J=15 Hz, 1H, 5.28, q, J=7 Hz, 1H, 7.20–7.40, m, 10H.

MS: (E.I. 70 ev) m/e 438 (13%), 423 (6%), 333 (16%), 187 (30%), 174 (15%), 105 (63%), 91 (100%).

Example F

Production of d-biotin

A solution of 100 mg of (3aS,6aR)-hexahydro-1-[(R)-(1-phenylethyl)]-2-oxo-3-benzylthieno[3,4-d]imidazole-4-ylidene pentanoic acid in 4 ml of hydrobromic acid (48 percent) was heated in a 25-ml round-bottom flask for 3 hours at 120° C. with a vacuum of 400 mbars. After the reaction mixture was cooled, it was extracted with 5 ml of toluene. Then the aqueous phase was distilled off in a vacuum. The residue was dissolved in 10 ml of water and extracted with 10 ml of chloroform at 60° C. The aqueous phase was concentrated to 1 ml and cooled. d-(+) biotin precipitated in 40 mg of beige crystals (72 percent yield). Concerning the product: Melting point: 227°–229° C.

$[\alpha]_D^{25}$ [c=0.1 1N NaOH] +84.5°.

What is claimed is:

1. Process for the production of an imidazole derivative of the formula:

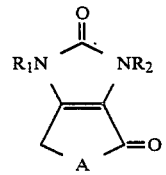

IX wherein R₁ is an (R)- or (S)-1-phenylalkyl group, an (R)- or (S)-1-alkoxycarbonyl-1-phenylmethyl group or an (R)- or (S)-aryloxycarbonyl-1-phenylmethyl group, R₂ is hydrogen, a substituted or unsubstituted alkanoyl group, a substituted or unsubstituted benzoyl group, a substituted or unsubstituted benzyl group, an alkoxycarbonyl group, an aryloxycarbonyl group, an alkoxyalkyl group, a pyranyl group, a substituted or unsubstituted benzenesulfonyl group, an alkylsulfonyl group, a diarylphosphinyl, group, a dialkoxyphosphinyl group or a trialkylsilyl group, and A is a sulfur or oxygen atom, comprising reacting a tetronic acid of the formula:

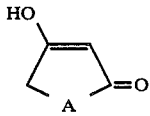

wherein A has the above-mentioned meaning, with a diazonium salt, converting the resultant arylazotetronic acid or the tautomeric arylhydrazone in a further step with a chiral amine into an arylazoamino compound, reducing the arylazoamino compound, converting the resultant diamine, with phosgene or a phosgene-equivalent reagent, into a corresponding imidazole and optionally introducing a protective group by reaction with a substituted or unsubstituted aliphatic or aromatic acid chloride, a benzyl halide, an aliphatic or aromatic carboxylic acid anhydride, a haloformic acid alkyl ester, a 1-alkoxyalkyl halide, an enol ether, an aromatic or aliphatic sulfonic acid halide, a diarylphosphinic acid halide, a phosphoric acid dialkyl ester halide, a trialkyl silyl halide or a trialkyl silyl acetamide.

2. Process according to claim 1, wherein a substituted benzene diazonium halide, a benzene boron tetrafluoride or a benzene hydrosulfate is used as the diazonium salt.

3. Process according to claim 2 wherein a (R)- or (S)-1-phenylalkylamine or a (R)- or (S)-2-aminophenyl acetic acid alkyl ester is used as the chiral amine.

4. Process according to claim 3 wherein an acid catalyst is used for the conversion to the arylazoamino compound.

5. Process according to claim 4 wherein the reduction is effected by catalytic hydrogenation with hydrogen or by reaction with zinc in the presence of hydrochloric acid or acetic acid.

6. Process according to claim 5, wherein the reduction is effected by hydrogenation in the presence of platinum, palladium, rhodium, ruthenium or Raney nickel.

7. Process according to claim 6 where the platinum, palladium, rhodium, ruthenium or Raney nickel is supported on carbon, clay, pumice, aluminum oxide or aluminum silicate.

8. Process according to claim 6, wherein as the phosgene equivalents there is used a compound of the formula:

YCOZ wherein Y and Z are the same and represent chlorine or imidazolyl, or Y is chlorine and Z is a substituted or unsubstituted alkoxy or a substituted or unsubstituted aryloxy.

9. Process according to claim 7 wherein the conversion to imidazole takes place in the presence of a base.

10. Process according to claim 8 wherein a tertiary amine is used as the base.

11. Process according to claim 1 wherein a (R)- or (S)-1-phenylalkylamine or a (R)- or (S)-2-aminophenyl acetic acid alkyl ester is used as the chiral amine.

12. Process according to claim 1 wherein an acid catalyst is used for the conversion to the arylazoamino compound.

13. Process according to claim 1 wherein the reduction is effected by catalytic hydrogenation with hydrogen or by reaction with zinc in the presence of hydrochloric acid or acetic acid.

14. Process according to claim 13 wherein the reduction is effected by hydrogenation in the present of platinum, palladium, rhodium, ruthenium or Raney nickel.

15. Process according to claim 1 wherein as the phosgene equivalents there is used a compound of the formula:

YCOZ wherein Y and Z are the same and represent chlorine or imidazolyl, or Y is chlorine and Z is a substituted or unsubstituted alkoxy or a substituted or unsubstituted aryloxy.

16. Process according to claim 8 wherein the conversion to imidazole takes place in the presence of a base.

17. Process according to claim 9 wherein a tertiary amine is used as the base.

* * * * *